(12) United States Patent
Igaki

(10) Patent No.: US 8,262,687 B2
(45) Date of Patent: Sep. 11, 2012

(54) STENT HOLDING MEMBER AND STENT FEEDING SYSTEM

(75) Inventor: Keiji Igaki, Kyoto (JP)

(73) Assignee: Kyoto Medical Planning Co., Ltd., Kyoto (JP)

( * ) Notice: Subject to any disclaimer, the term of this patent is extended or adjusted under 35 U.S.C. 154(b) by 1779 days.

(21) Appl. No.: 10/220,472

(22) PCT Filed: Apr. 27, 2001

(86) PCT No.: PCT/JP01/03742
§ 371 (c)(1),
(2), (4) Date: Aug. 30, 2002

(87) PCT Pub. No.: WO02/068037
PCT Pub. Date: Sep. 6, 2002

(65) Prior Publication Data
US 2003/0033001 A1 Feb. 13, 2003

(30) Foreign Application Priority Data
Feb. 27, 2001 (JP) ................... P2001-052716

(51) Int. Cl.
*A61M 29/00* (2006.01)
(52) U.S. Cl. ........................ 606/198; 623/1.11
(58) Field of Classification Search ............ 604/48, 604/96.01, 104, 106, 915; 606/108, 192, 606/194, 195, 198; 623/1.11, 1.12, 1.15, 623/1.16, 1.18, 1.2, 1.21, 1.38, 1.42, 1.43, 623/1.46, 1.54, 23.7
See application file for complete search history.

(56) References Cited

U.S. PATENT DOCUMENTS

| | | | | |
|---|---|---|---|---|
| 2,736,721 | A * | 2/1956 | Dexter | 525/475 |
| 4,370,358 | A * | 1/1983 | Hayes et al. | 427/515 |
| 4,921,483 | A * | 5/1990 | Wijay et al. | 604/103.1 |
| 5,116,318 | A | 5/1992 | Hillstead | |

(Continued)

FOREIGN PATENT DOCUMENTS
EP 0 894 505 A2 2/1999
(Continued)

OTHER PUBLICATIONS
European Search Report dated Jun. 15, 2004.

*Primary Examiner* — Tuan V Nguyen
(74) *Attorney, Agent, or Firm* — Rader, Fishman & Grauer PLLC

(57) ABSTRACT

A stent holding member used in a stent delivery system adapted to implant a stent of a cylindrical configuration, designed to be embedded in a living body, to a desired site of implantation in a vessel of the living body. The stent holding member includes a tubular holding member formed of an elastic material. The holder has a groove in its outer peripheral portion for holding one or more supporting struts making up the stent. Each of these supporting struts is embedded at least partially in the groove to hold the stent. The groove has its opening end side expanded by expansion of the holder along the radial direction. By expansion of the opened end of the groove, the stent held in the groove is dilated and released from the holder.

13 Claims, 7 Drawing Sheets

U.S. PATENT DOCUMENTS

| | | | |
|---|---|---|---|
| 5,634,901 A * | 6/1997 | Alba et al. | 604/96.01 |
| 5,688,516 A | 11/1997 | Raad | |
| 5,807,327 A * | 9/1998 | Green et al. | 623/1.11 |
| 5,817,100 A | 10/1998 | Igaki | |
| 5,913,871 A | 6/1999 | Werneth | |
| 5,976,155 A | 11/1999 | Foreman et al. | |
| 6,056,906 A * | 5/2000 | Werneth et al. | 264/135 |
| 6,066,156 A * | 5/2000 | Yan | 606/192 |
| 6,077,295 A | 6/2000 | Limon et al. | |
| 6,146,358 A * | 11/2000 | Rowe | 604/103.02 |
| 6,187,013 B1 * | 2/2001 | Stoltze et al. | 606/108 |
| 6,254,608 B1 * | 7/2001 | Solar | 606/108 |

FOREIGN PATENT DOCUMENTS

| | | |
|---|---|---|
| WO | 95/20992 | 8/1995 |
| WO | 95/33422 | 12/1995 |
| WO | WO-00/51525 A1 | 9/2000 |
| WO | WO-00/53123 A1 | 9/2000 |

* cited by examiner

STENT HOLDING MEMBER AND STENT FEEDING SYSTEM

TECHNICAL FIELD

The present invention relates to a stent holding member used in a stent delivery device for transferring a stent which is implanted in a vessel of a living body, such as a blood vessel, lymphatic vessel, bile duct or urinary tract, via e.g., a catheter, to set an expanded state the vessel and to maintain the expanded state for a preset time period, at a desired site of implantation in the vessel, and to a stent delivery device employing such a stent holding member.

BACKGROUND ART

Where the state of stenosis has occurred in a vessel of a living body, such as a blood vessel, or in particular an artery, the technique of percutaneous angioplasty (PTA) is routinely applied. This is the surgical procedure of introducing a balloon mounted to the vicinity of the distal end of a catheter to the stenosed lesion, with the balloon then being expanded to hold open the stenosed lesion to secure the blood flow.

It is known that, even with the application of PTA, there is a high risk of restenosis occurring in the stenosed lesion.

In order to prevent restenosis, a stent is implanted into the vessel to which PTA has been applied. The stent, implanted into the blood vessel in the constricted state, is subsequently dilated and implanted into the blood vessel to support the vessel wall from inside to prevent restenosis. Such stents formed of metal, e.g., stainless steel, Ti—Ni alloy, or of a resin material or of biodegradable polymer have already been proposed and are already known to be in use.

A stent delivery system is used for delivering the stent to a desired site in the vessel. The stent delivery system has a different stent holding mechanism, depending on the method used for expanding the stent.

For example, a stent delivery system exists in which a balloon expandable stent, contracted by plastic deformation, is expanded by a balloon and kept in the expanded state even after removal of the balloon. Therefore the stent may be implanted into a desired site in the vessel.

This stent delivery system comprises a balloon in a contracted state at the distal end of the catheter, and a mechanism for loading and holding a balloon-mounted stent, with the stent being in a contracted state under the effect of plastic deformation. The catheter carrying the balloon at its distal end, as used here, is termed a balloon catheter.

For implantation of the stent into a desired site, the stent delivery system comprising the balloon catheter and carrying the stent, is introduced into the vessel.

When the stent has been delivered to the desired site of implantation, a fluid material, such as a contrast medium, which is an X-ray impermeable liquid material, is supplied to the balloon via the catheter to dilate the balloon. Such expansion of the balloon dilates the stent mounted to the outer periphery of the balloon.

Another stent delivery system, a self-expandable stent, contracted under an external pressure and expanded on removal of the external pressure, to a desired site of implantation in the vessel, is provided with a mechanism for holding the stent by a protective sheath for preventing self-expandable of the stent. This protective sheath is adapted for covering the outer periphery of the stent, mounted in a contracted state to the distal end of the catheter inserted into a vessel of the living body. This stent delivery system holds the stent in the contracted state by means of the protective sheath and delivers the stent to the target site in the vessel without the stent incidentally becoming detached from the catheter. When the stent mounted to the distal end of the catheter has been delivered to the target site in the vessel, the protective sheath is moved relatively to the catheter, whereby the stent is expanded from the contracted state, so as to be self-expanded and left at the desired site in the vessel.

Meanwhile, the stent delivery system for the balloon expandable stent is of such a structure that the catheter carrying the stent exposed to the outer surface of the balloon is introduced into the vessel. Therefore, while the stent is being delivered to the site of implantation in the vessel, the stent tends to cause some injury to the inner wall of the vessel, as it comes into contact with the vessel wall directly. In particular, if the stent is delivered in the exposed state from the catheter or balloon to a target site in the blood vessel, which is of small diameter and is bent or meandering, the blood vessel wall coming into contact with the stent may readily be injured. Moreover, if the stent is made of metal, sharp or rigid sites may be produced on the surface of the stent. If the above-described stent is introduced into the vessel in the exposed state, the inner wall of the vessel may be easily injured. Additionally, in the stent delivery system for the balloon expandable stent, there are cases of the stent becoming detached from the stent delivery system during its delivery to the target site. This occurs when the balloon expandable stent is mounted directly on the balloon without the protective sheath.

In the stent delivery system for the self-expandable stent, the protective sheath is mounted on the outer periphery of the stent, which is loaded at the distal end of the catheter. Thus, the stent portion of the delivery system for the self-expandable stent is larger in outer diameter than the stent portion of the delivery system for the balloon expandable stent.

It is difficult to deliver the stent to a target site with a large outer diameter the stent delivery system and especially so if the desired target site has a small inner diameter. Furthermore it is impossible to implant the stent if the inner diameter of the desired target site is smaller than the outer diameter of the stent delivery system. Consequently, the self-expandable stent has limitations in terms of target site, as compared to the balloon expandable stent.

In the case whereby the stent delivery system for the self-expandable stent delivers the stent in a tortuous blood vessel, the protective sheath and the stent should be delivered together in the bent or meandering blood vessel. Therefore, it is difficult to remove the protective sheath smoothly from the stent and to implant the stent into the target site. Moreover it is extremely difficult to release the stent, loaded on the distal end of the catheter, from the contracted state brought about by the protective sheath, and to implant the stent thus released at the desired site in the vessel.

In order to introduce the stent into the vessel which is not only of small diameter and tortuous, but also is consolidation, the characteristics of the stent delivery system are needed to pass the stenosed site easily and with sufficient tractability, otherwise the stent will be unable to reach the desired target site.

Consequently, the shape and mechanical properties of the stent delivery system, which deliver the various types of stent to the desired target site, require a small outer diameter, flexibility and surface smoothness.

DISCLOSURE OF THE INVENTION

It is an object of the present invention to provide a stent holding member capable of positively implanting the stent loaded on the catheter to a desired site in the vessel of the living body, without the risk of detachment, and a stent delivery system employing this stent holding member.

It is another object of the present invention to provide a stent holding member capable of implanting the stent to a desired site in the vessel of the living body, without injuring the vessel wall, and a stent delivery system employing this stent holding member.

It is still another object of the present invention to provide a stent holding member which allows the stent to pass through the vessel of small diameter so as to be implanted in the vessel, and a stent delivery system employing this stent holding member.

It is still another object of the present invention to provide a stent holding member which allows the stent to pass through the tortuous or consolidated vessel of small diameter, and a stent delivery system employing this stent holding member.

It is still another object of the present invention to provide a stent holding member which enables the stent loaded on the catheter to be implanted accurately at a desired site in the vessel of the living body, and a stent delivery system employing this stent holding member.

It is yet another object of the present invention to provide a stent deliver and holding member which enables an optional stent to be readily combined with an optional balloon catheter.

For accomplishing the above object, the present invention provides a stent holding member used in a stent delivery system adapted to deliver a stent of a cylindrical configuration, designed to be implanted in a living body, to a desired site of implantation in a vessel, in which the stent holding member includes a tubular holding member formed of an elastic material. The holder has a groove in its outer peripheral portion for holding one or more supporting struts making up the stent. The struts are embedded at least partially in the groove to hold the stent.

The holder may also be formed of an elastic material, formed of, for example, a silicone resin based adhesive, exhibiting tackiness, in order to raise the holding power of the stent mounted on its outer periphery. By using the silicone-based adhesive, exhibiting tackiness, it is possible to improve the stent holding power to allow the holder to retain the stent even if the struts forming the stent are not fully embedded in the groove.

The groove holding the struts of the stent of the tubular structure has its open end expanded by expansion of the holder in the radial direction. By the expansion of the open end side of the groove, the holding power of the holder is lost, such that the stent held by the struts embedded in the groove is released from the holder. In case the silicone-based adhesive exhibiting tackiness is used, the tackiness is lowered due to expansion of the holder in the radial direction to release the stent from the holder.

By embedding part or all of the stent's struts, the stent can be held without excessively protruding from the outer periphery of the holder, so that, when the stent is inserted together with the holding member into the vessel, it is possible to prevent the stent from injuring the inner wall of the vessel.

The holder may be formed of one or more materials selected from the group consisting of synthetic resin, natural resin, silicon resin and silicone-based resin adhesive, those have the modulus of elasticity.

The holder is formed by layering two or more tubular members having different values of the modulus of elasticity. The tubular member of the outer layer may be formed by a silicon resin based adhesive exhibiting tackiness.

The present invention also provides a stent delivery system adapted to transfer a stent of a cylindrical configuration, designed to be implanted in a living body, to a desired site of implantation in a vessel of the living body. The stent delivery system includes a catheter inserted into a vessel of a living body, a balloon provided to the distal end of the catheter and expanded by a fluid supplied into the inside of the catheter, and a stent holding member provided to the outer periphery of the balloon. The holder has a groove in its outer peripheral portion for holding one or more supporting struts making up the stent. The struts are embedded at least partially in the groove to hold the stent.

The stent held by the stent holding member is released from the stent holding member and dilated by expansion of the holder in the radial direction on expansion of the balloon.

Other objects, features and advantages of the present invention will become more apparent from reading the embodiments of the present invention as shown in the drawings.

BEST MODE FOR CARRYING OUT THE INVENTION

Figure 1:
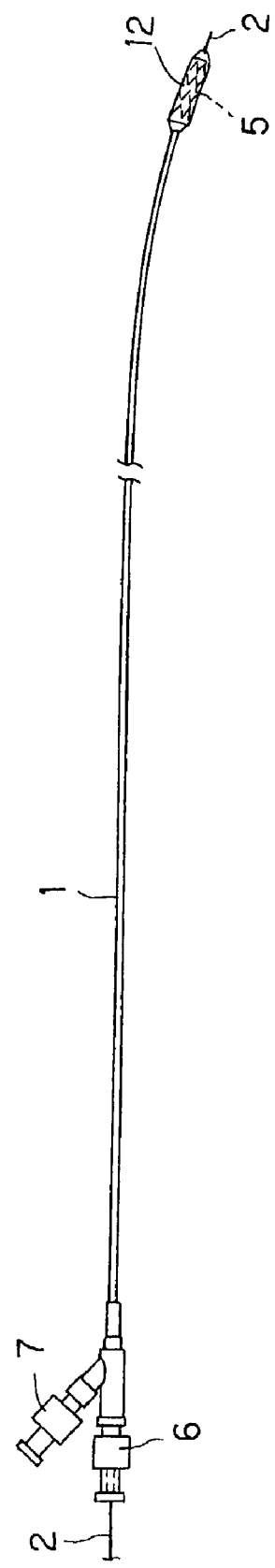
FIG. 1 is a perspective view showing a stent delivery system according to the present invention.

Referring to the drawings, a stent holding member and a stent delivery system employing this stent holding member according to the present invention will now be explained more specifically.

First, the stent delivery system employing the stent holding member according to the present invention is explained.

Figure 2:
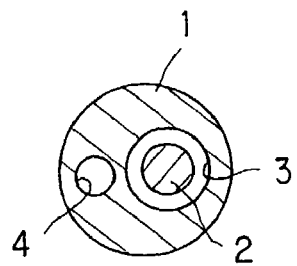
FIG. 2 is a cross-sectional view showing an instance of a catheter constituting the stent delivery system.

This stent delivery system includes a catheter 1, introduced into a vessel, such as a blood vessel, as shown in FIG. 1. The catheter 1 is formed of e.g., a flexible synthetic resin material, and includes a wire-introducing through-hole 3, adapted to be passed through by a guide wire 2, and a fluid passage 4 for supplying a fluid, such as a contrast medium, formed of an X-ray impermeable liquid material, as shown in FIG. 2. The through-hole 3 and the fluid passage 4 are arranged side-by-side relative to each other. The guide wire 2, inserted into the catheter 1, is introduced into the blood vessel in advance of the catheter 1 so as to serve as a guide to introduce the catheter 1 to a desired target site. The fluid supplied into the fluid passage 4 is used for expanding the balloon 5 mounted to the distal end of the catheter 1.

The proximal end of the catheter 1 includes a valving mechanism 6, for securing the wire 2 inserted into the wire-introducing through-hole 3 and for opening/closing the wire-introducing through-hole 3, and a fluid-supplying valving mechanism 7 for opening/closing the fluid passage 4 provided to the catheter 1, as shown in FIG. 1.

Figure 3:
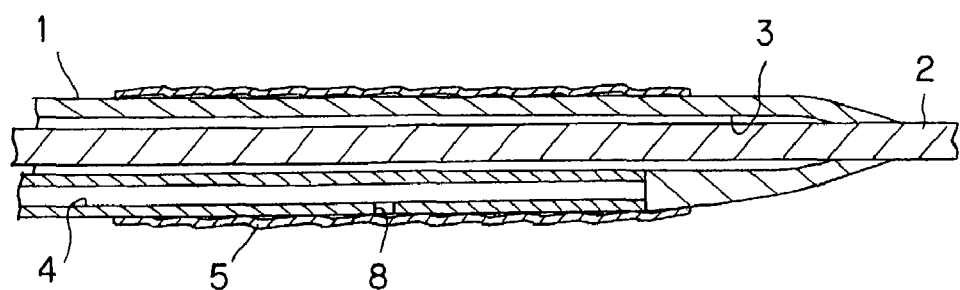
FIG. 3 is a partial cross-sectional view showing the vicinity of a distal end of the catheter provided with a balloon.

To the distal end of the catheter 1, there is mounted, in a contracted state, a balloon 5, which is expanded by the fluid supplied via the fluid passage 4, as shown in FIG. 3. In a portion of the catheter 1 to which to mount the balloon 5, there is bored one or more through-hole(s) 8 communicating with the fluid passage 4. The through-hole 8 has the function of supplying the fluid fed into the fluid passage 4 into the inside of the balloon 5 or of sucking the fluid, supplied into the balloon 5, via the fluid passage. The balloon 5 is mounted to the distal end of the catheter 1 to overlie the through-hole 8 as shown in FIG. 3, so that it is expanded by the fluid supplied into the fluid passage 4 to flow via the through-hole 8, and so that it is contracted by the fluid sucked back into the fluid passage 4 via the through-hole 8.

Meanwhile, the balloon 5 has its both ends bonded to the outer periphery of the catheter 1, such as with an adhesive, so as not to be disengaged from the catheter 1.

The balloon 5 is formed of e.g., polyethylene terephthalate (PFT) in the form of a thin film, and is designed to be expanded to a preset size as the fluid is supplied into its inside.

To the distal end of the catheter 1, carrying the balloon 5 as described above, there is mounted a stent holding member 12 holding the stent 11 on its outer periphery. The stent holding member 12 is mounted to cover the outer peripherla surface of the balloon 5, as shown in FIG. 4.

Figure 5:
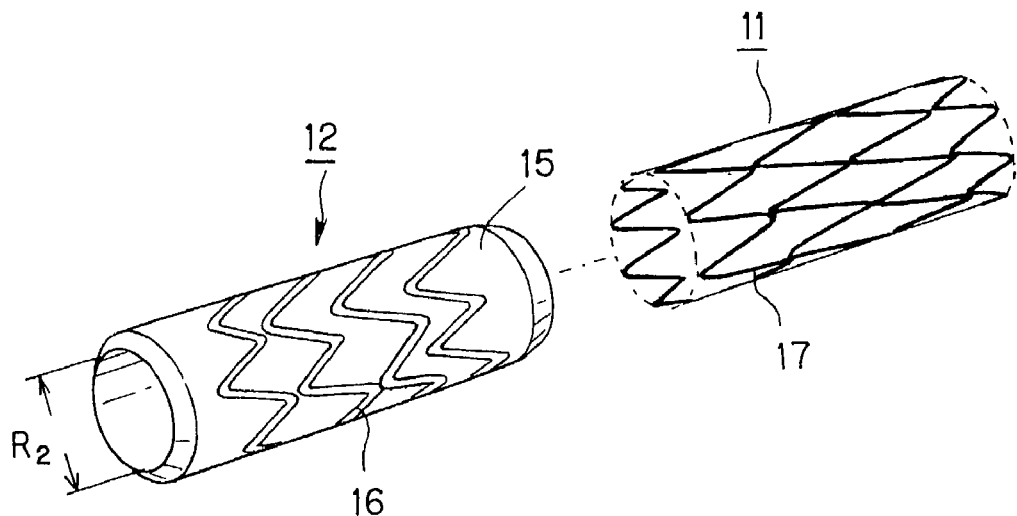
FIG. 5 is a perspective view showing a holder constituting a stent holding member according to the present invention and a stent retained by this holder.

The stent holding member 12 includes a tubular holder 15 having an outer peripheral groove 16 for holding the stent 11, as shown in FIG. 5. The holder 15 is formed of an elastic material that can be expanded or contracted to follow the expansion or contraction of the balloon 5. The holder 15 is formed of an elastic material that can be molded to the shape of the stent 11 held on its outer periphery. The elastic material may be synthetic resin, natural resin or silicone resin and specifically may be synthetic or natural rubber, silicone rubber or a silicone resin based adhesive.

Figure 4:
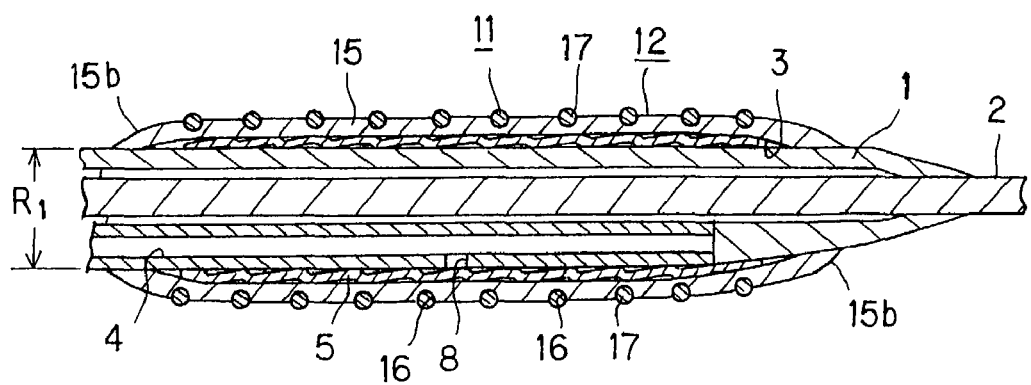
FIG. 4 is a cross-sectional view showing the state in which a stent holding member is mounted to the distal end of the catheter.

The holder 15 is in the form of a tube, havig an inner diameter R2 approximately equal to or slightly smaller than the outer diameter R1 of the catheter 1, so that the holder 15 can be mounted with a pressure fit to the outer peripheral surface of the balloon 5, which is collapsed around the outer peripheral surface of the catheter 1, in a manner to preclude inadvertent detachment, as shown in FIGS. 4 and 5. The holding member, formed by this holder and the stent, may also be used as a device that can be mounted to the balloon of a required guide catheter such as is disclosed in the specification and drawings of U.S. Pat. No. 5,817,100.

The groove 16, formed in the outer periphery of the holder 15, is designed to hold a filament, such as a fiber, as a supporting strut providing a skeleton structure forming the tubular stent 11 retained by the holder 15. Supposing that the stent 11 formed using the filament, such as fiber, is a male die, the groove is formed as a female die coincident in shape to the stent 11.

Turning more specifically to the stent 11, the stent 11 is formed by a fiber 17 of a biodegradable polymer, which is formed into a tubular, in particular a cylindrical shape, by spirally bending the fiber in a zig-zag pattern to present a series of concatenated V-shaped segments, as shown in FIG. 5.

The stent 11, formed using the fibers 17 of this biodegradable polymer, is formed as a self-expandable stent contracted under an external pressure and which may be dilated on removal of the external pressure.

The stent 11 may also be a self-expandable stent formed by an elongated metal filamant of, for example, Ti—Ni based alloy, which is formed into a tubular, in particular a cylindrical shape, and which, similarly to the fiber 17 of the biodegradable polymer, is wound spirally as it is bent in a zig-zag pattern to present a series of concatenated V-shaped segments.

Figure 6:
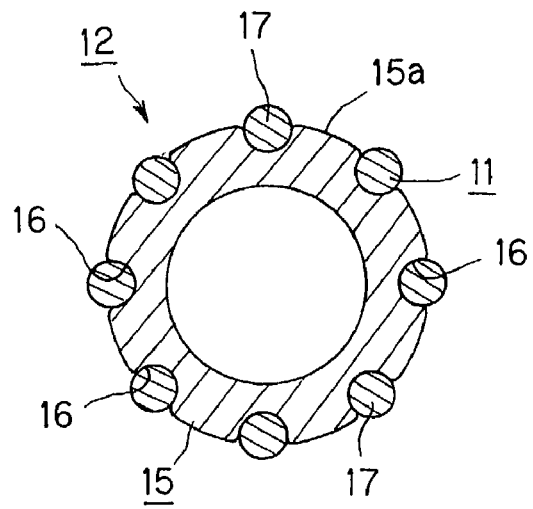
FIG. 6 is a cross-sectional view showing the stent holding member holding the stent.
Figure 7A:
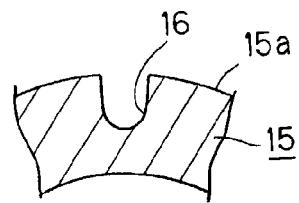
FIGS. 7A, 7B and 7C are partial cross-sectional views showing instances of grooves formed in the holder.
Figure 7B:
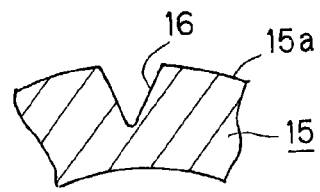
Figure 7C:
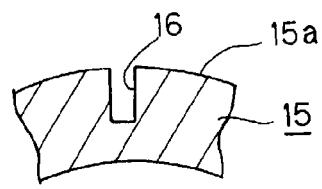

If a balloon expandable stent, not having the self-expandable power, is used, the holder is able to exhibit the function of holding the stent on its periphery even if the holder has no holding power sufficient to hold the self-expandable stent The groove 16, formed in the outer periphery of the holder 15, is formed in the outer periphral surface of the holder 15 so that about one half to a whole part of the cross-sectional profile of one fiber 17 as a supporting strut serving as a skeleton structure to maintain the shape of the stent 11 will be embedded in the groove, as shown in FIG. 6. The groove 16 is of a U-shape from an outer peripheral surface 15a towards the inside of the holder 15, as shown in FIG. 7A, of a V-shape from the outer peripheral surface 15a towards the inside of the holder 15, as shown in FIG. 7B, or of an I-shape from the outer peripheral surface 15a towards the inside of the holder 15, as shown in FIG. 7C, such as to enable the fiber 17 of the stent 11 to be embedded in or released from the groove 16. The groove 16 may be of any suitable shape on the condition that the fiber 17 of the stent 11 can be held embedded therein.

Although the groove 16 may be of variegated shape, it is formed to a width narrower than the outer diameter of the fiber 17 embedded in the groove 16. By having the width of the groove 16 narrower than the outer diameter of the fiber 17 embedded therein, the stent 11 can be held under exploitation of the elastic force proper to the holder 15.

The groove 16, formed in the outer peripheral surface 15a of the holder 15 as described above, is formed by engraving the holder, using a cutting device employing a laser beam, along the shape of the stent 11. Alternatively, there may be provided a die for molding which is in register with the stent 11 to be held so as to form the groove 16 using this die as a male die. The stent 11 itself, retained by the holder 15, may also be used as a die for forming the groove 16.

The stent 11 is embedded and retained in this state in the groove 16, without being excessively protruded from the outer peripheral surface 15a of the holder 15, by introducing the fiber 17 forming the tubular member into the groove 16 partially or entirely, as shown in FIG. 6. The stent 11, thus held, may be maintained in its contracted state, even if it is of the self-expandable type, that is, of the type in which it is dilated on removing the external pressure.

Since the stent holding member 12 according to the present invention holds the stent as it is embedded in the holder 15, the stent 11 may be positively prevented from becoming detached from the holder 15 when the stent holding member is mounted to the catheter 1 and introduced in this state into the blood vessel. Moreover, the stent 11 may be positively prevented from injuring the inner wall of the blood vessel to overcome the problem inherent in the delivering system for the balloon expandable stent.

Moreover, since it is unnecessary to provide a protective sheath required in a self-expandable stent, the stent holding member can pass through the vessel of small diameter reliably to enable the stent mounted to the catheter to be implanted acccurately at a desired site in the blood vessel in the living body.

It should be noted that, when the holder 15 is mounted on the catheter 1 and introduced in this state into the blood vessel, the holder 15 may directly contact the inner wall of the blood vessel. Therefore, the outer peripheral surface of the holder 15 is desirably smoothed so as not to injure the inner wall of the blood vessel when the holder 15 contacts the inner wall of the blood vessel during being introduced through the inside of the blood vessel. Additionally, both extreme ends of the holder 15 are formed as a tapered suface 15b or a smoothly continuously curved arcuate surface, as shown in FIG. 4.

Moreover, in order to prevent thrombi from becoming deposited on the stent holding member 12 or on the catheter 1 during introducing the stent holding member 12 through the inside of the blood vessel, an anti-thrombotic agent or the like pharmaceutical is desirably applied or deposited on the surface of the stent holding member 12 for holding the stent 11.

The stent holding member 12, constructed as described above, is mounted in position, such as by fitting to cover the outer peripheral surface of the balloon 5, mounted on the distal end of the catheter 1, as shown in FIG. 4. At this time, both ends of the stent holding member 12 covering the balloon 5 may be bonded to the catheter 1, using an adhesive. It should be noted that the site of bonding of the stent holding member 12 to the catheter 1 clears the balloon 5 so as not to obstruct the dilation of the balloon 5. As the bonding agent, fibrin starch, formed of a blood-based material exhibiting biocompatibility, or a cyanoacrylate-containing bonding agent, widely used at large as a skin forming agent for surgical use, may be used.

Figure 8:
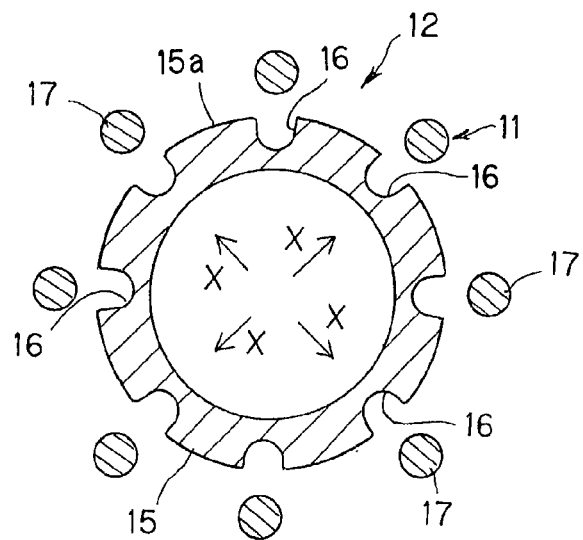
FIG. 8 is a cross-sectional view showing the state in which the holder is dilated to release the stent retained by the holder from the holder.
Figure 9:
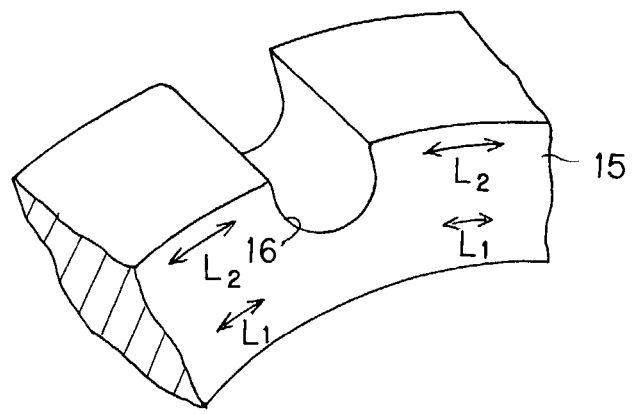
FIG. 9 is a perspective view showing the holder dilated to enlarge the groove.

With the stent holding member 12, constructed as described above, if the force acts from the inner periphery towards the outer periphery of the holder 15 as indicated by arrow X in FIG. 8, the holder 15 is enlarged in its outer diameter. The holder 15 is formed to a cylindrical shape, so that, if the holder 15 is enlarged in its outer diameter, an amount of expansion L2 on the outer periphery is larger than an amount of expansion L1 on the inner periphery, as shown in FIG. 9. Consequently, the groove 16 becomes deformed so that its open end is expanded to release the holding of the stent in the groove 16 to enable the stent 11 to be released from the holder 15. In case the stent 11 held by the holder 15 is of the self-expandable type, the stent is self-expanded and released from the holder 15. In case the stent 11 is the balloon expandable stent, the holder 15 is expanded and the stent is caused to be released from the holder 15 to expand the stent to its dilated state.

When the stent holding member 12 is mounted on a balloon catheter 1, the holder 15 is expanded by the expansion of the balloon 5.

The above explanation has been made with reference to the structure and efficacy of the stent holding member 12, methods for stent retention and release and to the manufacturing method as well as the component material. It should be noted that the holding power for the stent 11 may be further improved by exploiting the properties of the material of the holder 15. In such case, the holder 15 is formed of a silicone resin exhibiting tackiness. The silicone resin used is the singlesolution type silicone resin exemplified by 1215 (trade name) manufactured by Three-Bond Inc. By using the silicone resin, exhibiting tackiness, in preparing the holder 15, the stent 11 may be held more positively by the holder 15 by using both elasticity proper to the groove portion 16 of the holder and tackiness proper to the silicone resin.

In the case of the holder 15 formed of the silicone resin exhibiting tackiness, it is sufficient if the groove 16 is of such a depth that not more than one-half portion of the fiber 17 of the stent 11 is embedded therein, instead of being of such a depth that the fiber 17 is embedded therein in its entirety. Therefore, if the holder 15 is formed of the silicone resin, exhibiting tackiness, it is possible to prepare the stent holding member 12 of a smaller diameter and a higher flexibility.

The holder 15 of the above-described stent holding member 12 is formed of a unitary material, that is, the holder 15 is formed as a single-layer cylindrical member.

Meanwhile, it is desirable for the stent holding member 12 to hold the stent 11 positively when the stent holding member 12 is mounted on the catheter 1 and inserted in this state through the vessel, while it is also desirable for the stent holding member 12 to be expanded readily to follow the expansion of the balloon 5 in the process of expansion thereof.

Figure 10:
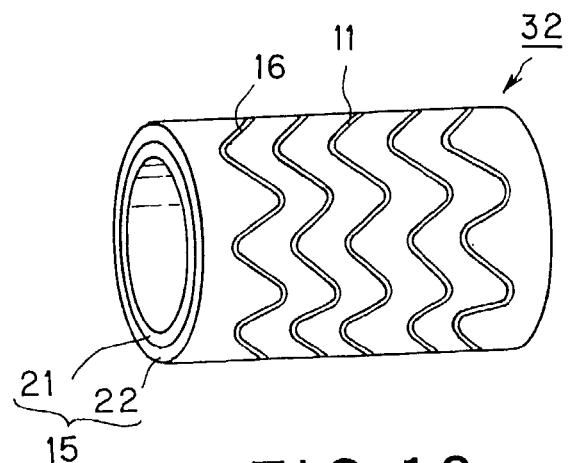
FIG. 10 is a perspective view showing a modification of the stent holding member according to the present invention.
Figure 11:
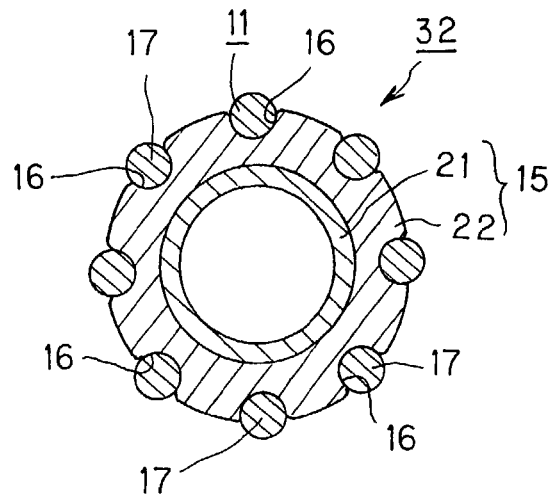
FIG. 11 is a cross-sectional view thereof.

Therefore, the holder 15 forming the stent holding member 12 is made up of first and second tubular members 21, 22, having at least different values of the modulus of elasticity, as shown in FIGS. 10 and 11. The second tubular member 22, provided on the outer peripheral side of the holder 15 of the two-layered structure, is formed of, for example, a silicone resin, having high elasticity and tackiness, to hold the stent 11 reliably in the groove 16 formed in its outer periphery. The first tubular member 21, provided on the inner periphery of the holder 15, is formed of a material of a modulus of elasticity which allows for uniform expansion of the material with the expansion of the balloon 5, such as natural or synthetic rubber. That is, the first tubular member 21 is formed of an elastic material lower in the modulus of elasticity than the materuial of the second tubular member 22.

Meanwhile, the groove 16, formed in the outer periphery of the second tubular member 22, is formed by a method similar to that for the groove formed in the aforementioned single-layer holder 15.

By using the silicone resin, exhibiting tackiness, in forming the second tubular member 22, the stent 11 can be retained more positively by the holder 15 by taking advantage not only of the support by the groove 16 but also of the tackiness proper to the silicone resin. As the material for the second tubular member 22, the single-solution type silicone resin, exemplified by 1215 (trade name) manufactured by Three-Bond Inc. may be used.

Figure 12A:
FIGS. 12A, 12B and 12C are perspective views showing the state of forming the holder constituting the stent holding member according to the present invention.
Figure 12B:
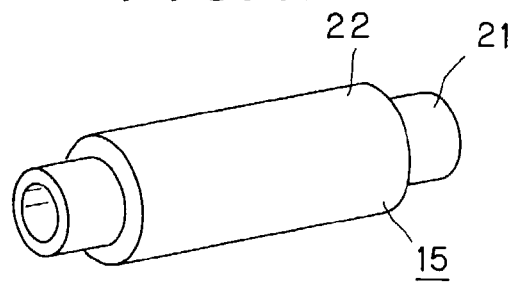
Figure 12C:
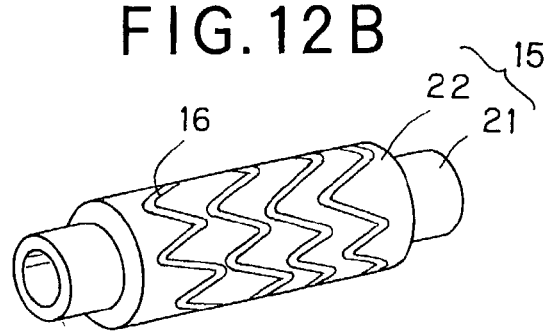

Meanwhile, a stent holding member 32, having the two-layered holder 15, may be manufactured by the following process steps:

First, a first tubular member 21, formed of natural or synthetic rubber, having an inner diameter sufficient for mounting the tubular member on the outer periphery of the balloon 5 provided on the catheter 1, is provided, as shown in FIG. 12A. A jellied silicone resin then is applied to the entire outer peripheral surface of the first tubular member 21, as shown in FIG. 12B, and dried in situ to form a solidified second tubular member 22. The groove 16 is formed as shown in FIG. 12C by providing a die for molding, corresponding to the stent 11 to be held by the second tubular member 22, and by pressing this die agaist the outer periphery of the second tubular member 22, during drying thereof, as shown in FIG. 12C. The stent 11 is embedded in the groove 16 to complete the stent holding member 32 comprised of the second tubular member 22 holding the stent 11.

It should be noted that the stent 11 itself may also be used as a die, without employing a die dedicated to groove forming.

The operational sequence of mounting the stent holding member 12 of the present invention to the catheter 1 of the stent delivery device and of implanting the stent 11 retained by the stent holding member 12 in the coronary vessel of the human body is now explained.

In the following explanation, it is assumed that the stent holding member 12 is such a one in which the holder 15 shown in FIGS. 5 and 6 is of a single-layer structure.

For implanting the stent 11 at a desired site in the coronary vessel, the catheter 1 carrying the stent holding member 12 holding the stent 11 is introduced into the coronary artery from the femoral artery or brachial artery of the patient. The catheter 1 at this time is inserted to a target site in the coronary vessel along a guide wire 2 which has already been introduced to the desired target site in the coronary vessel in advance of the catheter 1.

Figure 13:
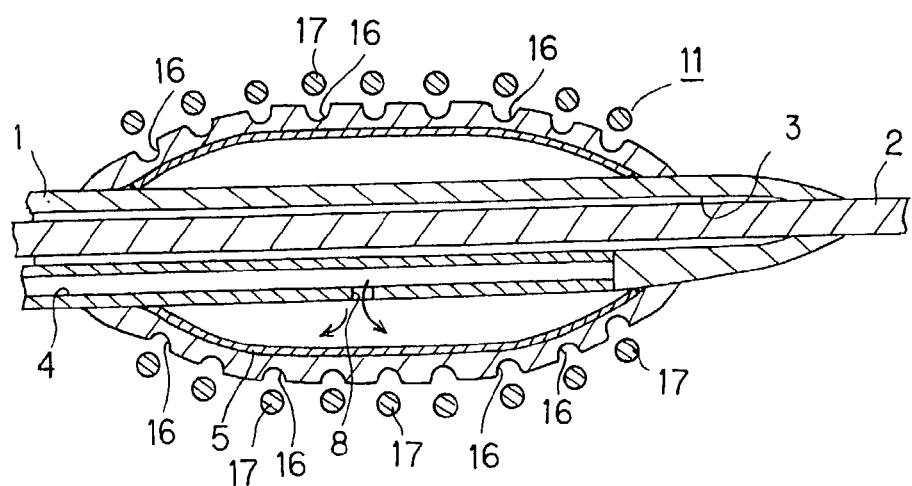
FIG. 13 is a longitudinal cross-sectional view showing the state in which the balloon provided to the catheter is expanded to dilate the holder to release the stent retained by the holder from the holder.
Figure 14:
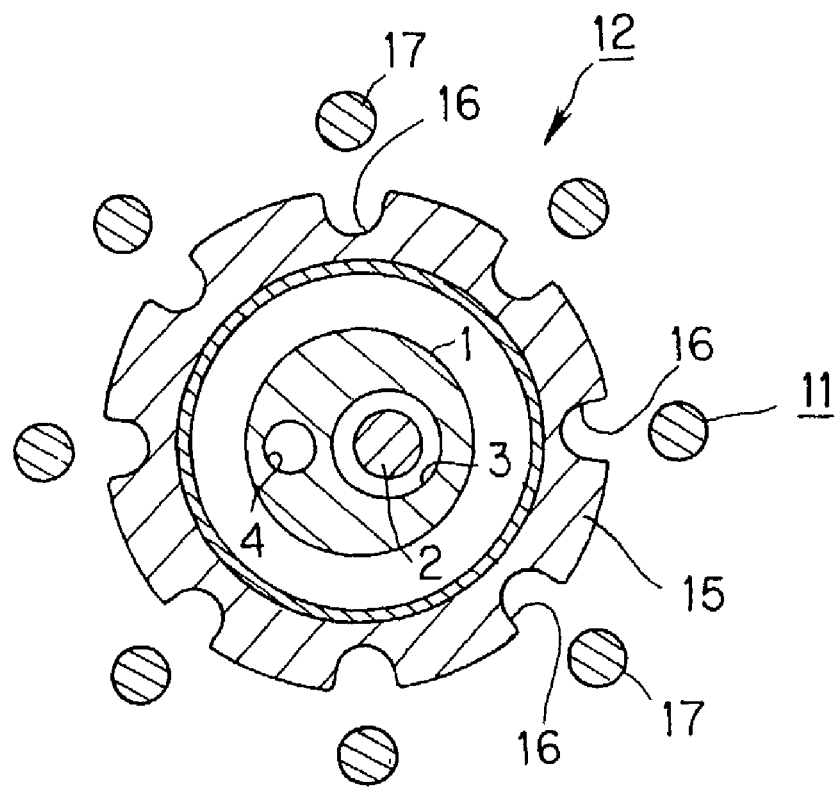
FIG. 14 is a transverse cross-sectional view thereof.

When it is confirmed that the catheter 1 has been introduced into the artery such that the stent holding member 12 has been inserted into the target site in the coronary vessel, the insertion of the catheter 1 is halted. Then, a fluid, such as an X-ray impermeable contrast medium, is injected into the fluid passage 4 via a valving mechanism 7 adapted for supplying the fluid. The fluid injected into the fluid passage 4 flows into the inside of the balloon 5 via the through-hole 8 to expand the balloon 5, as shown in FIGS. 13 and 14. When the balloon 5 is expanded, the holder 15 is expanded in outer diameter, as described above, so that the stent 11 is disengaged from the groove 16 to permit the stent 11 to be released from the holder 15. In case the stent 11 retained by the holder 15 is of the self-expandable type, the stent is dilated as it is self-expanded and released from the holder 15. In case the stent 11 is of the balloon expandable type, it is expanded to its dilated state as the holder 15 is expanded and as the stent is caused to be released from the holder 15.

If, after the stent 11 is released from the holder 15 and expanded, as described above, the fluid introduced into the balloon 5 is sucked via the fluid passage 4 to contract the balloon 5, the holder 15 is elastically deformed and contracted. Since the holder 15 is contracted, the stent 11, now dilated, is fully released from the holder 15, and is left by itself at a desired site in the coronary vessel. The stent 11 is finally implanted in the blood vessel by taking the catheter 1 out of the blood vessel following contraction of the balloon 5.

Meanwhile, in the case of the stent delivery device in which the stent holding member 2 shown in FIGS. 10 and 11 is mounted to the catheter 1, the stent 11 can be implanted to and left at a desired site in the vessel, such as coronary vessel, by a similar process of operations.

Figure 15:
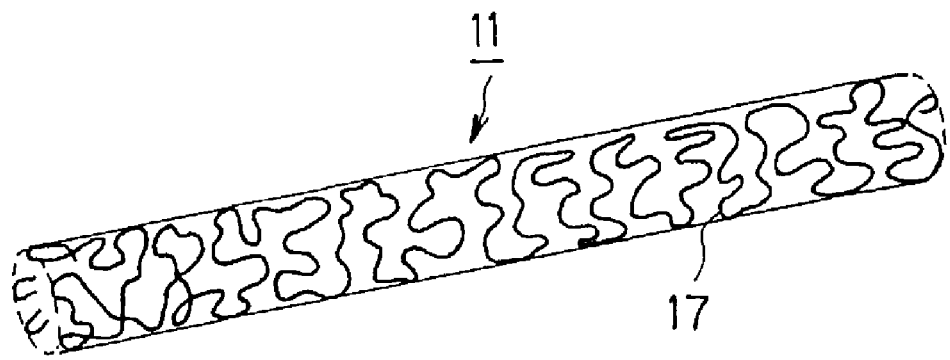
FIG. 15 is a perspective view showing a modification of a stent retained by the stent holding member according to the present invention.

The stent 11 retained by the stent holding member 12 of the present invention is not limited to the fiber 17 of biodegradable polymers or to a filament of a metal material which is wound spirally as it is bent in a zigzag pattern to form a sequence of concatenated continuous V-shaped segments. Thus, it may be formed by fibers 17 of a biodegradable polymer formed into a tubular shape, in particular a cylindrical shape, in a non-woven non-knitted state, as shown in FIG. 15. As another example of the stent 11, such a stent may be used which is obtained on applying diamond-meshed slicing to a sheet of a biodegradable polymer to form a sequence of consecutive supporting struts which may be expanded in a pantagraph fashion. Additionally, such a stent may also be used which is obtained on applying diamond-meshed slicing to a metal tube of stainless steel to form a sequence of consecutive supporting struts which may be expanded in a pantagraph fashion.

Industrial Applicability

According to the present invention, as described above, a stent is held embedded in a groove provided in a holder of a stent holding member, so that the stent may be implanted positively to a desired site in the vessel as inadvertent detachment of the stent is prevented form occurring. Moreover, there is no risk of the stent contacting and thereby injuring the inner wall of the vessel.

The stent holding member holds the stent without using a protective sheath into which the stent is inserted and retained, so that the stent holding member is able to pass through the vessel of a small diameter to get to a desired site of implantation.

Moreover, the holder used to retain the stent is formed of an elastic material which is flexible and deformable elastically, and hence the holder may be introduced smoothly through a tortuous vessel to reach the desired site of implantation.

The invention claimed is:

1. A stent holding member used in a stent delivery system adapted to introduce a stent of a cylindrical configuration, designed to be implanted in a living body, to a desired site of implantation in a vessel thereof, the stent holding member comprising:
   a tubular holder formed of a unitary elastic material, the tubular holder being mounted to the outer peripheral surface of a balloon of said stent delivery system prior to said stent being mounted to said tubular holder;
   said tubular holder having a groove in its outer peripheral portion for holding one or more supporting struts making up said stent, the groove being arranged for embedding each of said struts at least partially in said groove to hold the stent, said groove being formed to a width narrower than the outer diameter of said struts when the tubular holder is in a contracted state; and
   wherein said groove is arranged to have its opening end side expanded by expansion of said tubular holder along the radial direction to release the holding of the stent in the groove to enable the stent to be released from the tubular holder.

2. The stent holding member according to claim 1, further comprising an outer peripheral portion of said tubular holder, wherein said stent holding member holds a stent using said outer peripheral portion of said tubular holder by embedding said struts in said groove.

3. The stent holding member according to claim 1 wherein said tubular holder is formed of one or more selected from the group consisting of elastic synthetic resins, natural resins and silicone resins.

4. The stent holding member according to claim 1 wherein said tubular holder is formed of silicone resins exhibiting tackiness.

5. The stent holding member according to claim 1 wherein said tubular holder is formed by layering two or more tubular members having different values of modulus of elasticity.

6. The stent holding member according to claim 5 wherein the outer tubular member of said tubular holder is formed of a silicone resin.

7. The stent holding member according to claim 1, wherein said stent holding member holds a self-expandable stent which is contracted by applying an external pressure to said self-expandable stent and said stent holding member dilates said self-expandable stent when releasing said external pressure.

8. The stent holding member according to claim 1 wherein stent holding member holds a balloon expandable type stent.

9. The stent holding member according to claim 1 wherein said grooves in said outer peripheral portion of said tubular holder are formed to hold a tubular fiber of a biodegradable polymer which forms the strut.

10. The stent holding member according to claim 1, further comprising an anti-thrombotic agent deposited on the surface of said holder.

11. A stent delivery system adapted to introduce a stent of a cylindrical configuration designed to be implanted in a living body, to a desired site of implantation in a vessel thereof, the stent delivery system comprising:
- a catheter to be inserted into a vessel of a living body;
- a balloon provided to a distal end of said catheter and expanded by a fluid supplied into the inside of said catheter; and
- the stent holding member according to any one of claims 1 and 2-10, provided to said catheter for covering said balloon.

12. The stent delivery system according to claim 11 wherein said stent holding member releases and dilates said stent from said stent holding member by expansion of said holder along the radial direction brought about by expansion of said balloon.

13. The stent delivery system according to claim 11 wherein said stent holding member is mounted to said catheter, covering said balloon by having both ends bonded to said catheter.

* * * * *